(12) United States Patent
Sugimoto et al.

(10) Patent No.: US 10,905,510 B2
(45) Date of Patent: Feb. 2, 2021

(54) MANIPULATOR FOR DRIVING SURGICAL DEVICE THAT TREATS BODY TISSUE

(71) Applicant: Olympus Corporation, Hachioji (JP)

(72) Inventors: Arimasa Sugimoto, Hachioji (JP); Yuki Kikuchi, Nakano-ku (JP); Sadahiro Watanabe, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/366,285

(22) Filed: Mar. 27, 2019

(65) Prior Publication Data

US 2019/0216563 A1 Jul. 18, 2019

Related U.S. Application Data

(63) Continuation of application No. PCT/JP2017/013575, filed on Mar. 31, 2017.

(51) Int. Cl.
*A61B 17/00* (2006.01)
*A61B 34/00* (2016.01)
(Continued)

(52) U.S. Cl.
CPC .............. *A61B 34/70* (2016.02); *A61B 17/29* (2013.01); *A61B 46/10* (2016.02);
(Continued)

(58) Field of Classification Search
CPC .......... A61B 34/70; A61B 2017/00477; A61B 17/29; A61B 2090/0813; A61B 2034/301
See application file for complete search history.

(56) References Cited

U.S. PATENT DOCUMENTS 6,254,534 B1 7/2001 Butler et al.
2001/0037053 A1 11/2001 Bonadio et al.
(Continued)

FOREIGN PATENT DOCUMENTS

JP 2002-531160 9/2002
JP 2003-135385 5/2003
(Continued)

OTHER PUBLICATIONS

International Search Report and Written Opinion from corresponding International Application No. PCT/JP2017/013575, dated Jun. 13, 2017.

*Primary Examiner* — Muhammad S Islam
(74) *Attorney, Agent, or Firm* — Scully, Scott, Murphy & Presser, P.C.

(57) ABSTRACT

A manipulator is used to operate a surgical device that treats a body tissue. The manipulator includes a drive mechanism having a stationary section to be attached on a housing of a drive unit containing with at least one motor. A movable part is supported rotatably about a predetermined axis on the stationary section and having a connecting portion configured to be connected to the at least one motor when the stationary section is attached on the housing. A cover is configured to seal a gap between the movable part and the stationary section so as to prevent fluid from entering the gap between the movable part and the stationary part. A power transmission member is connected to both the movable part and the surgical device to transmit power from the motor to the surgical device.

26 Claims, 4 Drawing Sheets

(51) Int. Cl.
*A61B 17/29* (2006.01)
*A61B 46/10* (2016.01)
*A61B 90/00* (2016.01)
*A61B 34/30* (2016.01)

(52) U.S. Cl.
CPC .............. *A61B 2017/00477* (2013.01); *A61B 2017/2948* (2013.01); *A61B 2034/301* (2016.02); *A61B 2090/0813* (2016.02)

(56) References Cited

U.S. PATENT DOCUMENTS

| | | |
|---|---|---|
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0072762 A1 | 6/2002 | Bonadio et al. |
| 2003/0078478 A1 | 4/2003 | Bonadio et al. |
| 2004/0049100 A1 | 3/2004 | Butler et al. |
| 2004/0073090 A1 | 4/2004 | Arimilli et al. |
| 2004/0092795 A1 | 5/2004 | Bonadio et al. |
| 2004/0092796 A1 | 5/2004 | Butler et al. |
| 2004/0097793 A1 | 5/2004 | Butler et al. |
| 2004/0154624 A1 | 8/2004 | Bonadio et al. |
| 2004/0249248 A1 | 12/2004 | Bonadio et al. |
| 2005/0090716 A1 | 4/2005 | Bonadio et al. |
| 2005/0090717 A1 | 4/2005 | Clark |
| 2005/0192483 A1 | 9/2005 | Bonadio et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0240082 A1 | 10/2005 | Bonadio et al. |
| 2006/0247498 A1 | 11/2006 | Bonadio et al. |
| 2006/0247499 A1 | 11/2006 | Butler et al. |
| 2007/0004968 A1 | 1/2007 | Bonadio et al. |
| 2007/0093695 A1 | 4/2007 | Bonadio et al. |
| 2007/0203398 A1 | 8/2007 | Bonadio et al. |
| 2008/0097162 A1 | 4/2008 | Bonadio et al. |
| 2008/0097163 A1 | 4/2008 | Butler et al. |
| 2009/0292176 A1 | 11/2009 | Bonadio et al. |
| 2010/0063362 A1 | 3/2010 | Bonadio et al. |
| 2011/0092778 A1 | 4/2011 | Butler et al. |
| 2012/0029297 A1 | 2/2012 | Bonadio et al. |
| 2012/0065472 A1* | 3/2012 | Doyle .................... A61B 46/13 600/121 |
| 2012/0116172 A1 | 5/2012 | Butler et al. |
| 2012/0123214 A1 | 5/2012 | Bonadio et al. |
| 2013/0035697 A1 | 2/2013 | Ogawa et al. |
| 2013/0041219 A1 | 2/2013 | Hasegawa et al. |
| 2013/0066333 A1 | 3/2013 | Hyodo |
| 2013/0116509 A1 | 5/2013 | Bonadio et al. |
| 2013/0338646 A1 | 12/2013 | Butler et al. |
| 2014/0135795 A1 | 5/2014 | Yanagihara |
| 2014/0144258 A1 | 5/2014 | Kishi |
| 2014/0148817 A1 | 5/2014 | Hasegawa et al. |
| 2014/0148818 A1 | 5/2014 | Komuro et al. |
| 2014/0148819 A1 | 5/2014 | Inoue et al. |
| 2014/0148820 A1 | 5/2014 | Ogawa et al. |
| 2014/0148821 A1 | 5/2014 | Nakayama |
| 2014/0148950 A1 | 5/2014 | Ogawa et al. |
| 2014/0160015 A1 | 6/2014 | Ogawa et al. |
| 2014/0166023 A1 | 6/2014 | Kishi |
| 2014/0190305 A1 | 7/2014 | Okamoto |
| 2014/0257333 A1 | 9/2014 | Blumenkranz |
| 2014/0303443 A1 | 10/2014 | Bonadio et al. |
| 2014/0323809 A1 | 10/2014 | Bonadio et al. |
| 2014/0330079 A1 | 11/2014 | Ishizaki et al. |
| 2015/0068348 A1* | 3/2015 | Kirihara ............... B25J 19/0075 74/490.03 |
| 2015/0148611 A1 | 5/2015 | Bonadio et al. |
| 2015/0272563 A1 | 10/2015 | Butler et al. |
| 2016/0022257 A1 | 1/2016 | Bonadio et al. |
| 2016/0213366 A1 | 7/2016 | Butler et al. |
| 2016/0270774 A1 | 9/2016 | Butler et al. |
| 2016/0354108 A1 | 12/2016 | Nakano et al. |
| 2017/0325801 A1 | 11/2017 | Bonadio et al. |
| 2018/0116741 A1* | 5/2018 | Garcia Kilroy ...... B25J 15/0019 |

FOREIGN PATENT DOCUMENTS

| | | |
|---|---|---|
| JP | 2013-034833 | 2/2013 |
| JP | 2016-515847 | 6/2016 |
| JP | 2016-168220 | 9/2016 |
| JP | 2016-221081 | 12/2016 |
| WO | 2000032116 | 6/2000 |
| WO | 20130147017 | 10/2013 |
| WO | 20140010347 | 1/2014 |
| WO | 2014138365 | 9/2014 |

* cited by examiner

MANIPULATOR FOR DRIVING SURGICAL DEVICE THAT TREATS BODY TISSUE

CROSS-REFERENCE TO RELATED APPLICATIONS

This application is a continuation application of PCT Application No. PCT/JP2017/013575 filed Mar. 31, 2017, which is hereby incorporated by reference in its entirety.

TECHNICAL FIELD

The present disclosure generally relates to a manipulator and more particularly, to a manipulator used to drive a surgical device that treats a body tissue.

DESCRIPTION OF THE RELATED ART

Various devices such as endoscope having O-rings for sealing or fluid tightness purposes are known. For example, Japanese Patent JP 2016-168220A discloses an endoscope that includes an O-ring disposed between a rotating shaft and a cylindrical member for sealing a gap between the rotating shaft and the cylindrical member while ensuring slidability of the rotating shaft. However, due to complexity in structure of medical devices such as endoscope or the likes, any attempt to secure fluid tightness by an O-ring leads to difficulty in cleaning a narrow gap formed between parts, where the O-ring is disposed. Furthermore, when fluid tightness is secured by an O-ring, the slidability of a rotating shaft significantly varies depending on several factors such as the diameter of the rotating shaft, the materials of parts such as the rotating shaft and a cylindrical member, the O-ring, the amount of flattening of the O-ring, and so on.

Accordingly, there is a need for a manipulator that can facilitate cleaning by securing the fluid tightness of the manipulator while ensuring the slidability of a rotating shaft.

BRIEF SUMMARY OF EMBODIMENTS

One aspect of the present disclosure is directed to a manipulator being used to operate a surgical device that treats a body tissue and a drive mechanism that drives the surgical device. The drive mechanism includes a stationary section attached on a housing of a drive unit containing at least one motor. A rod-shaped movable part is supported rotatably about a predetermined axis on the stationary section. The rod-shaped movable part includes a second connecting portion configured to be connected to the at least one motor when the stationary section is attached on the housing. A cover seals, a gap between the movable part and the stationary section in a fluid-tight state. The cover includes a first cover part, a cylindrical second cover portion, and a torsion absorbing portion being integrally attached to the first cover part and a cylindrical second cover portion. The first cover part covers the stationary section around the movable part. The cylindrical second cover portion covers an outer peripheral surface of the movable part and attached in a close contact state on the outer peripheral surface. The torsion absorbing portion is configured to absorb a torsion caused by rotation of the second cover portion associated with rotation of the movable part.

In use, the surgical device is driven by attaching the stationary section of the drive mechanism onto the housing of the drive unit and attaching the second connecting portion of the movable part to the motor. The motor drives the surgical device via the movable part. The gap between the movable part and the stationary section is sealed in the fluid-tight state by the cover so as to prevent fluid or other dirt's entering the gap between the movable part and the stationary section. Therefore, this configuration significantly improves the cleanability of the drive mechanism.

It should be noted that when the movable part of the drive mechanism rotates about the predetermined axis under drive by the motor, the second cover portion also rotates about the predetermined axis as well, and therefore a torsion is developed between the second cover portion and the first cover part covering the stationary section. However, the torsion by the rotation of the second cover portion is absorbed at the torsion absorbing portion, thereby making it possible to avoid a reduction in the slidability of the movable part. As a consequence, the cleaning of the manipulator is facilitated by securing the fluid tightness of the manipulator while ensuring the slidability of the movable part.

In the above-described aspect, the torsion absorbing portion may be formed by folding back an end portion of the second cover portion over an entire periphery thereof in a direction along the axis thereof.

When configured as described above, the torsion absorbing portion permits twisting of the second cover portion about the axis thereof as much as the length of the folded-back portion at its end portion. By the torsion absorbing portion, the second cover portion is allowed to smoothly rotate following rotation of the movable part about the predetermined axis and thereby making it possible to sufficiently maintain the slidability of the movable part. Alternatively, the torsion absorbing portion may be formed by folding back an end portion of the second cover portion over an entire periphery thereof in a direction intersecting the axis thereof.

When configured as described above, the torsion absorbing portion permits twisting of the second cover portion about the axis thereof as much as the length of the folded-back portion at its end portion, so that the second cover portion is allowed to smoothly rotate following rotation of the movable part about the predetermined axis.

In the above-described aspect, the second cover portion may be bonded over an entire periphery thereof to the outer peripheral surface of the movable part with an adhesive.

When configured as described above, the close contact state of the second cover portion with the movable part can be maintained to improve the fluid tightness.

Figure 4:
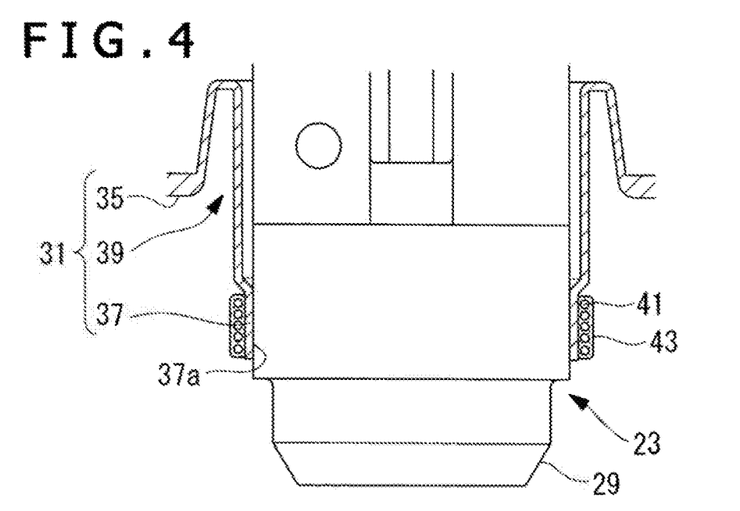
FIG. 4 is a vertical cross-sectional view illustrating a configuration of the cover that covers a rotation input part in the drive mechanism in FIG. 1.
Figure 5:
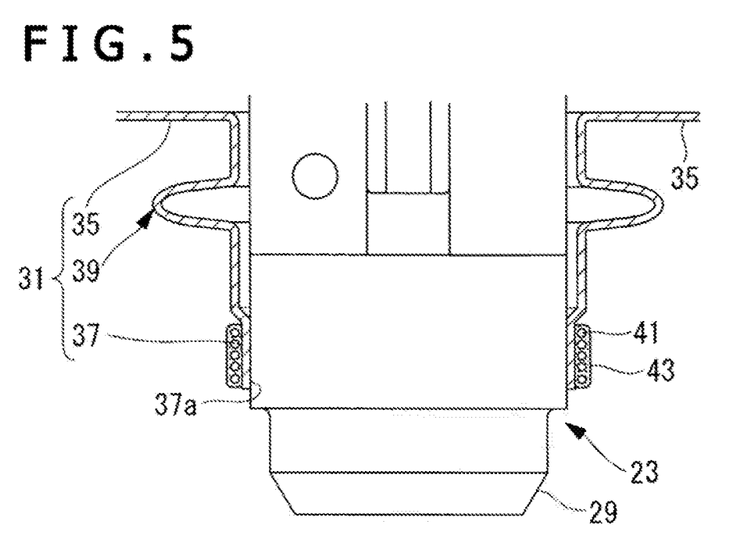
FIG. 5 is a vertical cross-sectional view illustrating a configuration of a modification of the cover in FIG. 4.

In the above-described aspect, a thread or cord is adhesively wrapped around the entire periphery of the outer peripheral surface of the second cover portion and is pressed against the outer peripheral surface of the movable part so as to securely hold the second cover portion to the movable part. The thread or cord generally resembles a winding coil as depicted in FIGS. 4 and 5 and substantially improves the fluid tightness between the second cover portion and the movable part.

The cover may include a rubber cover part made of a rubber material and having the first cover part, the second cover portion, and the torsion absorbing portion. A frame-shaped resin cover part made of a resin material and disposed along and over an entire periphery of an edge of the rubber cover part, fixed in a close contact state on the stationary section of the drive mechanism.

When the gap between the movable part and the stationary section is maintained in a fluid-tight state by the first cover part and the second cover portion of the rubber cover part, the slidability of the movable part of the drive mechanism sufficiently secured due to the elastic deformations of the torsion absorbing portion and the cover is securely attached to the stationary section of the drive mechanism by the frame-shaped resin cover part.

The manipulator may further include a power transmission member connected at one end to the movable part and at an opposite end to the surgical device with an elongated insert section extending from the stationary section of the drive mechanism in a direction intersecting the predetermined axis. The surgical device is generally disposed on a tip of the insert section, and the power of the motor is transmitted from the movable part to the surgical device via the power transmission member.

The stationary section of the drive mechanism is mounted on the housing of the drive unit in such a direction that a longitudinal axis of the insert section intersects an axis of rotation of the motor.

Figure 1:
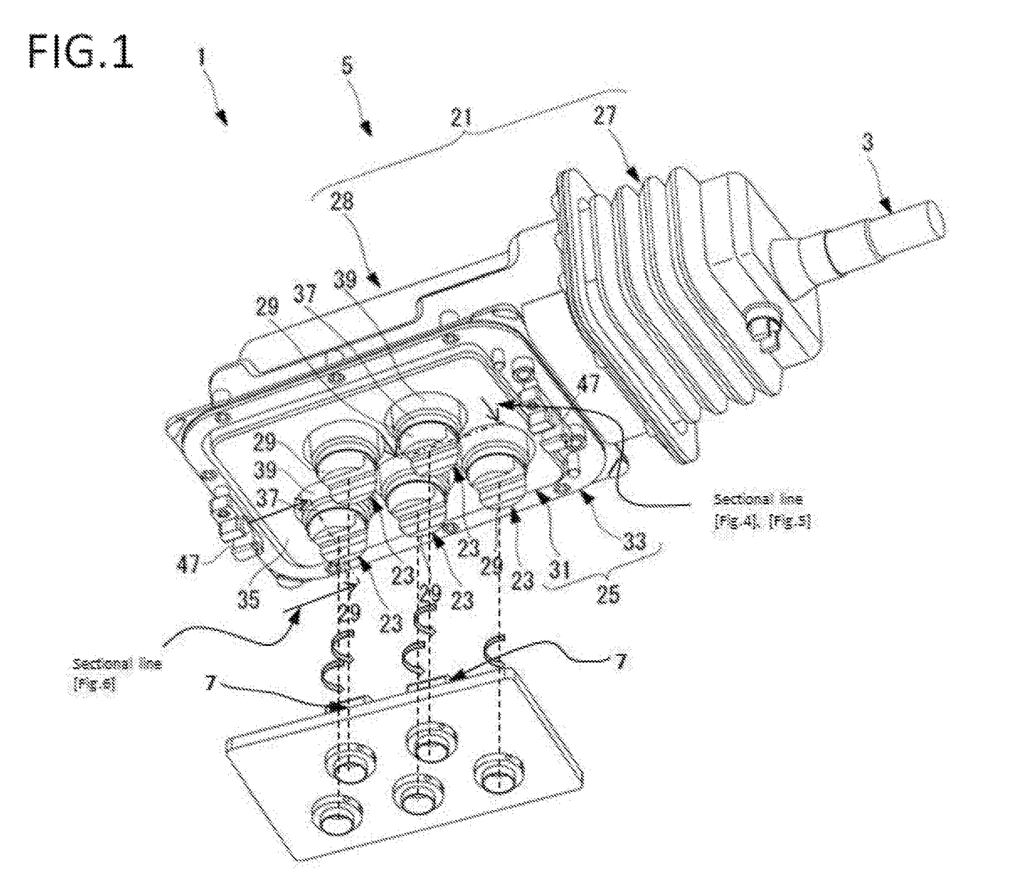
FIG. 1 is a perspective view of a manipulator having a drive unit detached according to an embodiment of the present invention.
Figure 6:
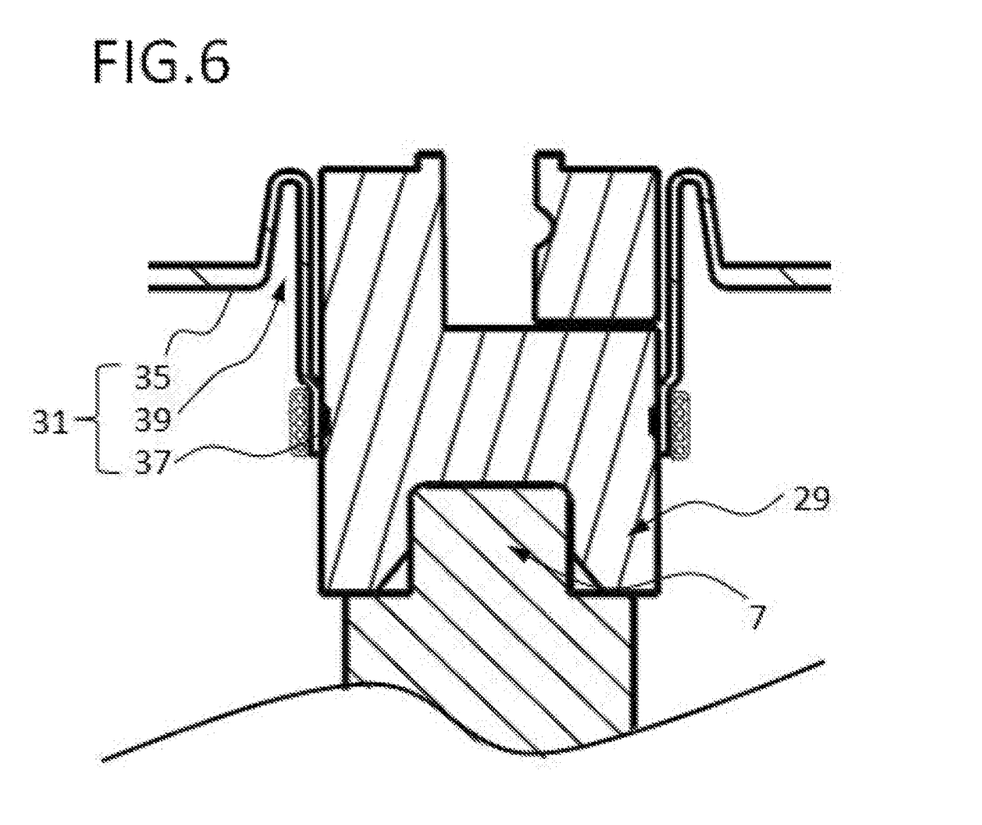
FIG. 6 is a perspective view of the manipulator of FIG. 1 having the drive unit of FIG. 2 mounted thereto.

In one exemplary embodiment depicted in FIG. 1, the drive mechanism includes a plurality of movable parts which correspond to the plurality of first connecting portions. Each of the plurality movable parts is engaged with the corresponding first connection portion as depicted in FIG. 6. As one of the ordinary skill in the art would appreciate that the number of the plurality of the movable parts corresponding to the number of the first connecting portion may be different depending on the specific configuration. The cover may include the first cover part and may also include a like plurality of second cover portions and torsion-absorbing portions as defined above. Each second cover portion may cover the outer peripheral surface of the associated movable part. Each torsion-absorbing portion may be disposed between the associated second cover portion and the first cover part and may be configured to absorb a torsion to be caused by rotation of the second cover portion.

The surgical device can be operated in various ways by the plurality of movable parts of the drive mechanism. In this case, fluid tightness is secured for each movable part by the associated second cover portion of the cover, and a torsion caused by rotation of each second cover portion associated with rotation of the associated movable part about the predetermined axis is absorbed by the associated torsion absorbing portion. Consequently, the cleaning of the manipulator is facilitated by securing the fluid tightness of the manipulator while ensuring the slidability of the individual movable parts. The second connecting portion of each movable part may have a recessed shape or a projecting shape.

The present disclosure can bring about advantageous effects that the cleaning of a manipulator can be facilitated by securing its fluid tightness while ensuring the slidability of the movable part, for example, a rotation input part.

BRIEF DESCRIPTION OF DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. The structural elements having the same functions are given the same reference signs throughout the drawings. Thus, features and advantages of the present disclosure will become more apparent from the following detailed description of exemplary embodiments thereof taken in conjunction with the accompanying drawings.

DETAILED DESCRIPTION OF THE EMBODIMENTS

A manipulator according to an embodiment of the present disclosure will hereinafter be described with reference to the drawings.

Figure 2:
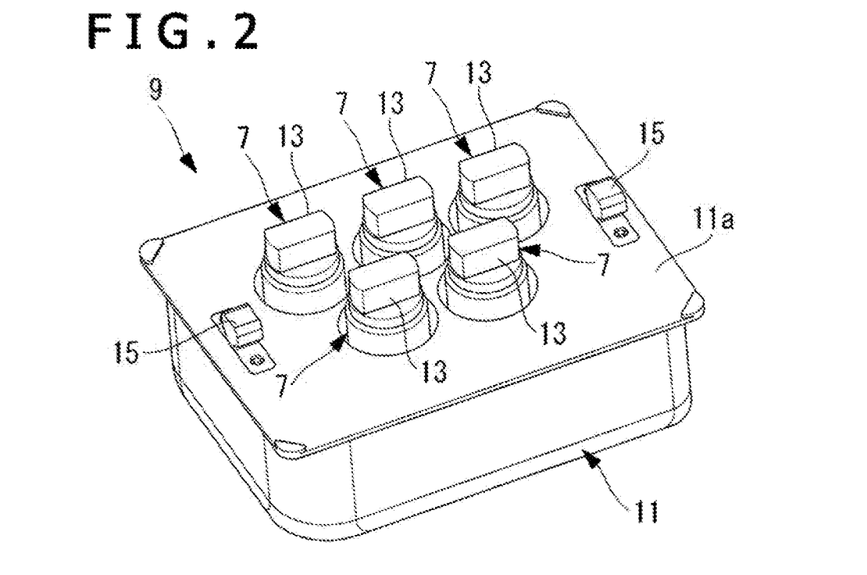
FIG. 2 is a top perspective view of a drive unit being attached on the manipulator of FIG. 1.

As illustrated in FIG. 1, the manipulator 1 according to the present embodiment includes an elongated insert section 3, a surgical devices, and a drive mechanism 5. The insert section 3 is inserted into the body of a patient. The surgical device is disposed on one end or tip of the insert section 3. Other end of the insert section 3 is attached to a drive mechanism 5 that is positioned on the side of a proximal end of the insert section 3 and drives the surgical device. The manipulator 1 can be mounted, for example, on a drive unit 9 including a plurality of motors 7 as illustrated in FIG. 2, so that the surgical device can be driven by drive force or forces or power of one or more of the motors 7.

Firstly, the drive unit 9 will be described with reference to FIG. 2.

The drive mechanism 9 is provided with five motors 7 each of which having a rotating shaft, which are parallel to one another and are positioned within a housing 11 via mounting surface 11a accommodating these motors 7 therein.

Each motor 7 has a first connecting portion 13 of a projecting shape at a tip of its rotating shaft, which is to be connected to the drive mechanism 5 of the manipulator 1. Furthermore, the motors 7 are supported rotatably about their axes of rotation independently of one another, with their connecting portions 13 extending out in directions along their axes of rotation from a mounting surface 11a of the housing 11. The motors 7 can be selectively actuated by a user via a control unit (not shown in Figures) and, for example, can be rotated in a range of approximately ±30 degrees about their axes of rotation.

The housing 11 of the drive unit 9 includes two ledge members 15 to be connected to the drive mechanism 5 of the manipulator 1. These two ledge members 15 are arranged at an interval therebetween on the mounting surface 11a of the housing 11, with the motors 7 being interposed between the ledge members 15.

Figure 3:
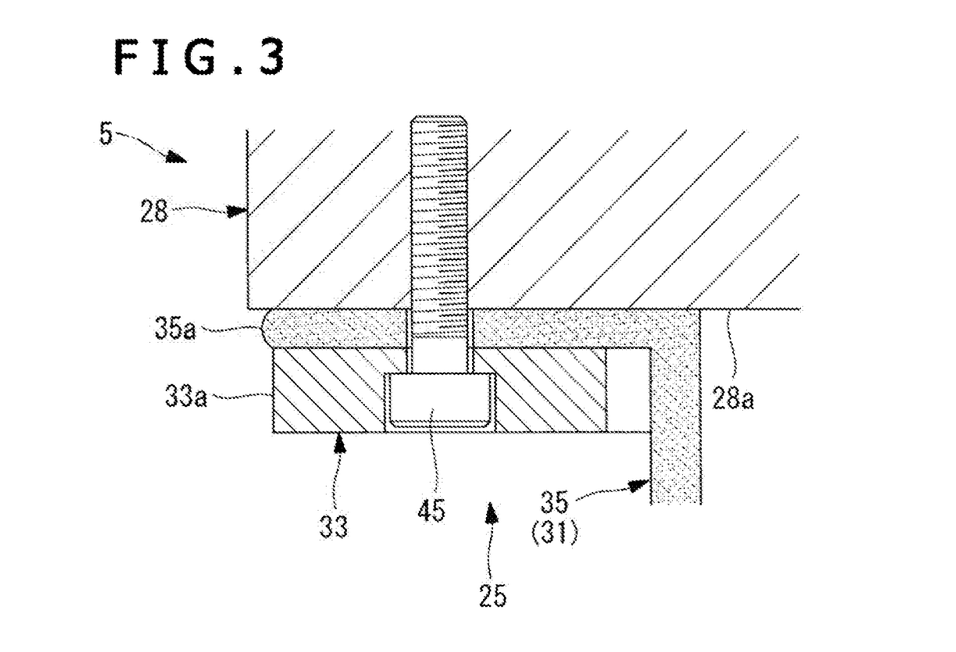
FIG. 3 is a vertical cross-sectional view of a fixed part of a mounting surface of a housing main body section and a cover in FIG. 1.

Referring to FIGS. 1, 3, and 4, the manipulator 1 will next be described in detail.

As illustrated in FIG. 1, the insert section 3 is connected at a longitudinally proximal end portion thereof to the drive mechanism 5. A plurality of wires (power transmission members, not shown in Figures) is connected at one ends thereof to the surgical device and are accommodated extending through the insert section 3.

The surgical device has, for example, a rotational joint turnable about a longitudinal axis of the insert section 3 and a plurality of flexing joints bendable in directions intersecting the longitudinal axis of the insert section 3, and is provided at a tip thereof with an end effecter such as grasping forceps or hot biopsy forceps. These rotational joint, flexing joints, and end effecter are configured to be driven independently of one another by tensions of the wires.

The drive mechanism 5 includes a housing 21, a plurality ("five" in the present embodiment) of rod-shaped rotation input parts or movable parts 23 and a cover 25. The housing 21 is mounted on the housing 11 of the drive unit 9. The rotation input parts or movable parts 23 are supported rotatably about mutually parallel axes thereof on the housing 21, and the power transmission members or wires are connected at opposite ends thereof to the rotation input parts or movable parts 23. The cover 25 seals gaps between the rotation input parts 23 and the housing 21 in a fluid-tight state.

The housing 21 of the drive mechanism 5 includes a concertina-shaped bellows section 27 to which the insert section 3 is connected, and a housing main body section or stationary section 28 of a substantially rectangular shape which is detachably attached on the housing 11 of the drive unit 9.

The bellows section 27 is configured to be deformable that enables to follow movements of the insert section 3 in directions intersecting the longitudinal axis of the insert section 3. The bellows section 27 is connected, in a close contact state, to the housing main body section 28 so that an interior of the bellows section 27 is in communication with an interior of the housing main body section 28.

Each rotation input part or movable part 23, at a tip thereof in a direction along an axis thereof, has a connecting portion 29 of a recessed shape configured to be connected to the connecting portion 13 of the corresponding motor 7 of the drive unit 9. These rotations input parts or movable parts 23 are disposed with their axes intersecting the longitudinal axis of the insert section 3.

Furthermore, these rotation input parts or movable parts 23 are supported rotatably independent from one another about their axes of their rotation such that portions thereof, which include the corresponding connecting portions 29, extend out in the directions along their axes from a mounting surface 28a as depicted in FIG. 3. The connecting portion 29 of each rotation input part or movable part 23 is configured to be connected to the first connecting portion 13 of the corresponding motor 7 when the housing main body section 28 of the drive mechanism 5 is mounted on the housing 11 of the drive unit 9.

The cover 25 is configured to cover the mounting surface 28a of the housing main body section 28 of the drive mechanism 5. The cover 25 includes a rubber cover part 31 of a substantially rectangular shape and a resin cover part 33 of a frame shape. The rubber cover part 31 is made of a rubber material and the resin cover part 33 is made of a resin material and is disposed along and over an entire periphery of an edge of the rubber cover part 31.

The rubber cover part 31 includes a first cover part 35, cylindrical second cover portions 37, and torsion absorbing portions 39. The first cover part 35 covers the mounting surface 28a of the housing main body section 28 around the respective rotation input parts 23. Each of the second cover portion 37 is cylindrical, covers the outer peripheral surface of the corresponding rotation input part 23, and is fixed, in a close contact state, on the outer peripheral surface of the corresponding rotation input part 23. Each torsion absorbing portion 39 is configured to absorb a torsion caused by rotation of the corresponding second cover portion 37 associated with rotation of the corresponding rotation input part 23 about the axis of rotation thereof.

As illustrated by way of example in FIG. 3, the first cover part 35 is disposed with a space to the mounting surface 28a of the housing main body section 28, and is configured to cover substantially the entire area of the mounting surface 28a. Furthermore, the first cover part 35 has an edge portion 35a, which is held over an entire periphery thereof in a stacked state between the mounting surface 28a of the housing main body section 28 of the drive mechanism 5 and the resin cover part 33.

The edge portion 35a of the first cover part 35 has substantially equal contour dimensions as the resin cover part 33. The edge portion 35a is configured to outwardly extend over an entire periphery thereof beyond an outer edge portion 33a of the resin cover part 33 in a state that the edge portion 35a is arranged between the housing main body section 28 of the drive mechanism 5 and the resin cover part 33. Consequently, it is possible to prevent soil, dirt, or fluid from entering the spacing between the housing main body section 28 of the drive mechanism 5 and the resin cover part 33.

As illustrated in FIG. 4, each of the second cover portion 37 has an opening 37a at a free end thereof in a direction along the axis of the associated rotation input part or movable part 23, and is configured such that the connecting portion 29 of the rotation input part 23 can be passed in a fluid-tight state from the opening 37a. Furthermore, each of the second cover portion 37 is wound at an outer peripheral surface thereof over an entire periphery thereof with a thread and is pressed at an inner peripheral surface thereof against the outer peripheral surface of the associated rotation input part 23. This configuration resembles a coil 41 of the wound thread that is fixed on the outer peripheral surface of the rotation input part 23 with an adhesive 43. Consequently, the second cover portion 37 is provided with enhanced pressing force to the rotation input part 23 to significantly improve the fluid tightness.

As illustrated in FIG. 4, each torsion absorbing portion 39 is integrally connected to the first cover part 35 and the associated second cover portion 37. The torsion absorbing portion 39 is formed by allowing an end portion of the second cover portion 37, the end portion being on the side of a proximal end of the second cover portion 37, to extend toward a proximal end of the rotation input part 23 without being fixed on the outer peripheral surface of the rotation input part 23 and then folding it back once over an entire periphery thereof in the direction along the axis of the second cover portion 37. As a consequence, the torsion absorbing portion 39 is configured to efficiently undergo an elastic deformation as much as its length, which extends in the direction along the axis of the torsion absorbing portion 39, plus the length of the folded back portion, whereby the torsion absorbing portion 39 is twisted about the axis thereof to permit twisting of the second cover portion 37 about the axis thereof.

As illustrated in FIG. 3, the resin cover part 33 is configured to be attached on the housing main body section 28 of the drive mechanism 5 by bolts 45 fastened to the mounting surface 28a of the housing main body section 28, with the edge portion 35a of the first cover part 35 of the rubber cover part 31 being held between the outer edge portion 33a and the mounting surface 28a of the housing main body section 28 of the drive mechanism 5.

As illustrated in FIG. 1, the resin cover part 33 has two latch members 47 to be brought into engagement with the ledge members 15 on the housing 11 of the drive unit 9. The latch members 47 have a shape complementary to the ledge members 15 on the drive unit 9, and are arranged at an interval therebetween on the resin cover part 33, with the rubber cover part 31 being interposed between the latch members 47.

A description will now be made about operations of the manipulator 1 configured as described above.

When desired to actuate the manipulator 1 according to the present disclosure, while firstly bringing the latch members 47 on the resin cover part 33 of the drive mechanism 5 into engagement with the ledge members 15 on the housing 11 of the drive unit 9, the connecting portions 29 of the individual rotation input parts 23 are connected to the connecting portions 13 of the corresponding motors 7, whereby the drive mechanism 5 is mounted on the drive unit 9.

One or more of the motors 7 of the drive unit 9 are next selectively actuated by a control unit (not shown) to rotate them in the range of approximately ±30 degrees about their axes of rotation. Then, the corresponding one or more of the rotation input parts 23 of the drive mechanism 5, is connected to the connecting portions 13 of the one or more motors 7, are rotated about the axes thereof, thereby power of the one or more motors 7 are transmitted to the surgical device via the corresponding one or more rotation input parts 23 and wires. As a consequence, the corresponding one or more of the rotational joint, flexing joints, and end effecter of the surgical device, to which the power of the one or more motors 7 have been transmitted, are driven.

In the drive mechanism 5, the gaps between the individual rotation input parts 23 and the housing main body section 28 are sealed in a fluid-tight state by the cover 25. It is, therefore, possible to prevent fluid from entering the gaps between the individual rotation input parts 23 and the housing main body section 28.

Since one of the rotation input parts 23 of the drive mechanism 5 is rotated about the axis thereof by power of the corresponding motor 7 and the second cover portion 37 is attached to the rotation input part 23 is also rotated about the axis thereof, then a torsion is developed between the second cover portion 37 and the first cover part 35.

In this situation, the torsion absorbing portion 39 of the cover 25 is twisted about the axis thereof through an elastic deformation, whereby the torsion developed by the rotation of the second cover portion 37 is absorbed to avoid a reduction of the slidability of the rotation input part 23. Hence, according to the manipulator 1 of the present embodiment, cleaning is facilitated by securing the fluid tightness of the drive mechanism 5 with the cover 25 while ensuring the slidability of the rotation input parts 23 of the drive mechanism 5.

In one embodiment, the first cover part 35 of the cover 25 is disposed with the spacing relative to the mounting surface 28a of the housing main body section 28. By pressing each second cover portion 37 around its outer peripheral surface in a direction that the first cover part 35 is moved closer to the mounting surface 28a of the housing main body section 28, the folded-back portion at the one end of the second cover portion 37, the folded-back portion forming the torsion absorbing portion 39, is hence allowed to undergo an elastic deformation, thereby enabling to widen a groove-shaped crevice at the folded-back portion. Therefore, soil or other dirt at the folded-back portion of the torsion absorbing portion 39 is readily cleaned off.

Each torsion absorbing portion has been described by exemplifying the torsion absorbing portion 39 of the configuration that as illustrated in FIG. 4, the one end portion of the second cover portion 37 is folded back in the direction along the axis of the second cover portion 37. However, the torsion absorbing portion 39 may have any configuration insofar as a torsion to be caused between the first cover part 35 and the second cover portion 37 by rotation of the second cover portion 37 can be absorbed. As illustrated in FIG. 5, for example, the torsion absorbing portion may be one formed by making the one end portion of the second cover portion 37 extend toward the proximal end of the rotation input part 23 without being fixed on the outer peripheral surface of the rotation input part 23, and further, by folding back a portion of the extended portion over an entire periphery thereof in a direction intersecting the axis of the second cover portion 37.

When modified, each torsion absorbing portion 39 can efficiently undergo an elastic deformation about the axis thereof as much as its length, which extends in the direction along the axis of the torsion absorbing portion 39, plus the length of the folded back portion, whereby the torsion absorbing portion 39 is twisted about the axis thereof to permit twisting of the second cover portion 37 about the axis thereof. By the torsion absorbing portion 39 illustrated in FIG. 5, the second cover portion 37 is also allowed to smoothly rotate following rotation of the rotation input part 23 about the axis thereof thereby making it possible to avoid a reduction of the slidability of the rotation input part 23.

Each torsion absorbing portion 39 has been described by exemplifying the torsion absorbing portion 39 of the configuration that the one end portion of the second cover portion 37, the one end portion being on the side of the proximal end of the second cover portion 37, is folded back once. However, the torsion absorbing portion may have any configuration insofar as twisting of the second cover portion 37 about the axis thereof is permitted through an elastic deformation of the folded-back portion. For example, the torsion absorbing portion may be formed by folding back an end portion of the second cover portion 37, the end portion being on the side of the proximal end of the second cover portion 37, a plurality of times over an entire periphery thereof.

Each of the second cover portion 37 is configured with the opening 37a. Insofar as the connecting portion 29 of each of the rotation input part 23 of the drive mechanism 5 and the connecting portion 13 of the corresponding motor 7 can be securely connected together. The opening 37a may be omitted from the second cover portion 37 and the connecting portion 29 of the rotation input part 23 may also be covered with the second cover portion 37.

Each of the second cover portion 37 is wound with the thread to resemble a shape of a coil 41 that is fixed on the outer peripheral surface of the rotation input part 23 with the adhesive 43. It is, however, required for the second cover portion 37 to be fixed in a fluid-tight state on the outer peripheral surface of the rotation input part 23. For example, the second cover portion 37 may be adhered, at the inner peripheral surface thereof and over the entire periphery thereof, to the outer peripheral surface of the rotation input part 23. This modification can more easily maintain the close contact state of the second cover portion 37 with the rotation input part 23.

The connecting portion 29 of each rotation input part 23 is configured with the recessed shape. It is, however, required for the connecting portion 29 of the rotation input part 23 to have a shape complementary to the connecting portion 13 of the corresponding motor 7. For example, the connecting portion 29 of the rotation input part 23 may have a projecting shape, while the connecting portion 13 of the motor 7 may have a recessed shape. Further, these connecting portions 29 and 13 may also be configured to have other shapes.

The present disclosure is not limited to the aforementioned Embodiments and the variation thereof, and various disclosure can be formed by appropriately combining plurality of components disclosed in the respective embodiments and the variation. For example, some components may be eliminated from all the components illustrated in each embodiment or the variation thereof, or components illustrated in different embodiments and the variation thereof may be combined appropriately.

One aspect of the disclosed technology is directed to a manipulator used to operate a surgical device that treats a body tissue. The manipulator comprises a drive mechanism having a stationary section to be attached on a housing of a drive unit containing at least one motor. A movable part is supported rotatably about a predetermined axis on the stationary section and having a second connecting portion configured to be connected to the at least one motor when the stationary section is attached on the housing. A cover is configured to seal a gap between the movable part and the stationary section so as to prevent fluid from entering the gap between the movable part and the stationary part.

The cover includes a first cover part covering the stationary section around the movable part. A cylindrical second cover portion covering an outer peripheral surface of the movable part and is fixed in a close contact state on the outer peripheral surface. A torsion absorbing portion is integrally connected to the cylindrical second cover portion and the first cover part and is configured to absorb a torsion caused by rotation of the cylindrical second cover portion associated with rotation of the movable part. The torsion absorbing portion is formed by folding back an end portion of the cylindrical second cover portion over an entire periphery thereof in a direction along the predetermined axis. The torsion absorbing portion is formed by folding back an end portion of the cylindrical second cover portion over an entire periphery thereof in a direction intersecting the predetermined axis thereof. The cylindrical second cover portion is adhesively bonded over an entire periphery thereof to the outer peripheral surface of the movable part. The cylindrical second cover portion is wound with a thread over an entire periphery of an outer peripheral surface thereof and is pressed against the outer peripheral surface of the movable part so that the thread resembles a coil that is adhesively attached on the outer peripheral surface of the movable part. The cover includes a rubber cover part made of a rubber material and having the first cover part, the cylindrical second cover portion, and the torsion absorbing portion. A frame-shaped cover part is made of a resin material and is disposed along and over an entire periphery of an edge of the rubber cover part and is fixed in a close contact state on the stationary section of the drive mechanism. The manipulator further comprises a power transmission member connected at one end thereof to the movable part and at an opposite end thereof to the surgical device. An elongated insert section extends from the stationary section of the drive mechanism in a direction intersecting the predetermined axis. The surgical device is disposed on a tip of the elongated insert section and power of the at least one motor is transmitted from the movable part to the surgical device via the power transmission member. The second connecting portion of the movable part has a recessed shape or a projecting shape.

Another aspect of the disclosed technology is a manipulator comprises a drive unit defined by a housing having a plurality of the motors attached thereto. Each of the plurality of the motors includes a first connecting portion projected outwardly therefrom. A drive mechanism is configured to be mounted onto the drive unit. The drive mechanism comprises a stationary section having a plurality of movable parts being supported rotatably and being projected outwardly from the stationary section. Each of the plurality of the movable part is attached to the corresponding first connecting portion when the drive unit is engaged with the drive mechanism. A cover is configured to seal a gap between the movable part and the stationary section so as to prevent fluid from entering the gap between the movable part and the stationary part. The cover is defined by a rubber cover part and a frame-shaped resin cover part disposed along and over an entire periphery of an edge of the rubber cover part. The rubber cover part includes a first cover part covering the stationary section around the movable part. A cylindrical second cover portion covering an outer peripheral surface of the movable part and is attached onto the outer peripheral surface. A torsion absorbing portion is integrally connected to the cylindrical second cover portion and the first cover part and is configured to absorb a torsion caused by rotation of the cylindrical second cover portion associated with rotation of the movable part. The drive unit includes two ledge members each of which is attached to respective ends of the housing. The drive mechanism includes two latch members each of which engaged with respective ledge members when the drive mechanism and the drive unit are attached to one another. Each of the plurality of the movable parts includes a respective second connecting portion having a recess formed therein. The manipulator is attached to a surgical device to treat a body tissue. The manipulator further comprising a power transmission member configured to be connected at one end to the plurality of movable parts and at an opposed end to a surgical device so as to transmit power from the plurality of the motors to the surgical device.

A further aspect of the disclosed technology is directed to a manipulator used to operate a surgical device that treats a body tissue. The manipulator comprises a drive unit defined by a housing having a plurality of the motors attached thereto. Each of the plurality of the motors includes a corresponding first connecting portion projected outwardly therefrom. A drive mechanism is configured to be mounted onto the drive unit. The drive mechanism comprises a stationary section having a plurality of movable parts being supported rotatably and being projected outwardly from the stationary section. Each of the plurality of the movable parts includes a respective second connecting portion each of which having a recess formed therein. Each of the respective second connecting portion is attached to the corresponding first connecting portion when the drive unit is engaged with the drive mechanism. A cover is defined by a rubber cover part and a frame-shaped resin cover part disposed along and over an entire periphery of an edge of the rubber cover part. The cover is configured to seal a gap between the movable part and the stationary section so as to prevent fluid from entering the gap between the movable part and the stationary part.

While various features are presented hereinabove, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A manipulator being used to operate a surgical device that treats a body tissue, the manipulator comprising:
   a drive mechanism comprising a first housing to be attached on a second housing of a drive unit containing at least one motor,
   a movable shaft being supported rotatably about a rotation axis on the first housing, the movable shaft having a portion configured to be connected to the at least one motor when the first housing is attached on the second housing, and
   a cover configured to seal a gap between the movable shaft and the first housing so as to prevent fluid from entering the gap between the movable shaft and the first housing;
   wherein the cover comprises:
      a first cover covering the first housing around the movable shaft;
      a cylindrical second cover covering an outer peripheral surface of the movable shaft and fixed in a close contact state on an outer peripheral surface of the movable shaft; and
      a torsion absorbing portion integrally connected to the cylindrical second cover and the first cover, the torsion absorbing part being configured to absorb a torsion caused by rotation of the cylindrical second cover associated with rotation of the movable shaft; and
      the torsion absorbing portion is formed by folding back an end portion of the cylindrical second cover over an entire periphery of the movable shaft in one of a direction along the rotation axis or in a direction intersecting the rotation axis.

2. The manipulator of claim 1, further comprising:
   a power transmission connected at one end thereof to the movable shaft and at an opposite end thereof to the surgical device; and
   an elongated insert section extending from the first housing in a direction intersecting the rotation axis,
   wherein the surgical device is disposed on a tip of the elongated insert section, and
   power of the at least one motor is transmitted from the movable shaft to the surgical device via the power transmission.

3. The manipulator of claim 1, wherein the portion of the movable shaft has one of a recess or a projection.

4. A manipulator comprising:
   a drive unit comprising a first housing having a plurality of motors disposed in the first housing, each of the plurality of the motors includes a first connecting portion projected outwardly from the first housing; and
   a drive mechanism configured to be mounted onto the drive unit, the drive mechanism comprises a second housing having a plurality of movable shafts supported rotatably on the second housing, the plurality of movable shafts being projected outwardly from the second housing and wherein each of the plurality of movable shafts being coupled to a corresponding first connecting portion when the drive unit is engaged with the drive mechanism, and
   a cover being configured to seal a gap between each of the plurality of movable shafts and the second housing so as to prevent fluid from entering the gap between each of the plurality of movable shafts and the second housing;
   wherein the cover comprises a rubber cover and a frame-shaped resin cover disposed along and over an entire periphery of an edge of the rubber cover.

5. The manipulator of claim 4, wherein the rubber cover includes
   a first cover covering the second housing around each of the plurality of movable shafts;
   a cylindrical second cover covering an outer peripheral surface of each of the plurality of movable shafts and being attached onto the outer peripheral surface; and
   a torsion absorbing portion integrally connected to the cylindrical second cover and the first cover, the torsion absorbing part being configured to absorb a torsion caused by rotation of the cylindrical second cover associated with rotation of each of the movable shafts.

6. The manipulator of claim 4, wherein the drive unit includes two ledge members each of which being attached to respective ends of the first housing.

7. The manipulator of claim 6, wherein the drive mechanism includes two latch members each of which being configured to engage with a corresponding one of the two ledge members when the drive mechanism and the drive unit are attached to one another.

8. The manipulator of claim 4, wherein each of the plurality of movable shafts includes a second connecting portion comprising a recess.

9. The manipulator of claim 4, wherein the drive mechanism is attached to a surgical device to treat a body tissue.

10. The manipulator of claim 4, further comprising a power transmission configured to be connected at one end to the plurality of movable shafts and at an opposed end to a surgical device so as to transmit power from the plurality of motors to the surgical device.

11. A manipulator being used to operate a surgical device that treats a body tissue, the manipulator comprising:
    a drive mechanism comprising a first housing to be attached on a second housing of a drive unit containing at least one motor,
    a movable shaft being supported rotatably about a rotation axis on the first housing, the movable shaft having a portion configured to be connected to the at least one motor when the first housing is attached on the second housing, and
    a cover configured to seal a gap between the movable shaft and the first housing so as to prevent fluid from entering the gap between the movable shaft and the first housing;
    wherein the cover comprises:
       a first cover covering the first housing around the movable shaft;
       a cylindrical second cover covering an outer peripheral surface of the movable shaft and fixed in a close contact state on an outer peripheral surface of the movable shaft; and
       a torsion absorbing portion integrally connected to the cylindrical second cover and the first cover, the torsion absorbing part being configured to absorb a torsion caused by rotation of the cylindrical second cover associated with rotation of the movable shaft; and wherein the cylindrical second cover is adhesively bonded over an entire periphery to the outer peripheral surface of the movable shaft.

12. The manipulator of claim 11, further comprising:
a power transmission connected at one end thereof to the movable shaft and at an opposite end thereof to the surgical device; and
an elongated insert section extending from the first housing in a direction intersecting the rotation axis,
wherein the surgical device is disposed on a tip of the elongated insert section, and
power of the at least one motor is transmitted from the movable shaft to the surgical device via the power transmission.

13. The manipulator of claim 11, wherein the portion of the movable shaft has one of a recess or a projection.

14. A manipulator being used to operate a surgical device that treats a body tissue, the manipulator comprising:
a drive mechanism comprising a first housing to be attached on a second housing of a drive unit containing at least one motor,
a movable shaft being supported rotatably about a rotation axis on the first housing, the movable shaft having a portion configured to be connected to the at least one motor when the first housing is attached on the second housing, and
a cover configured to seal a gap between the movable shaft and the first housing so as to prevent fluid from entering the gap between the movable shaft and the first housing;
wherein the cover comprises:
a first cover covering the first housing around the movable shaft;
a cylindrical second cover covering an outer peripheral surface of the movable shaft and fixed in a close contact state on an outer peripheral surface of the movable shaft; and
a torsion absorbing portion integrally connected to the cylindrical second cover and the first cover, the torsion absorbing part being configured to absorb a torsion caused by rotation of the cylindrical second cover associated with rotation of the movable shaft; and
wherein the cylindrical second cover is wound with a thread over an entire periphery of an outer peripheral surface of the movable shaft and is pressed against the outer peripheral surface of the movable shaft such that the thread is coiled and adhesively attached around the outer peripheral surface of the movable shaft.

15. The manipulator of claim 14, further comprising:
a power transmission connected at one end thereof to the movable shaft and at an opposite end thereof to the surgical device; and
an elongated insert section extending from the first housing in a direction intersecting the rotation axis,
wherein the surgical device is disposed on a tip of the elongated insert section, and
power of the at least one motor is transmitted from the movable shaft to the surgical device via the power transmission.

16. The manipulator of claim 14, wherein the portion of the movable shaft has one of a recess or a projection.

17. A manipulator being used to operate a surgical device that treats a body tissue, the manipulator comprising:
a drive mechanism comprising a first housing to be attached on a second housing of a drive unit containing at least one motor,
a movable shaft being supported rotatably about a rotation axis on the first housing, the movable shaft having a portion configured to be connected to the at least one motor when the first housing is attached on the second housing, and
a cover configured to seal a gap between the movable shaft and the first housing so as to prevent fluid from entering the gap between the movable shaft and the first housing;
wherein the cover comprises:
a first cover covering the first housing around the movable shaft;
a cylindrical second cover covering an outer peripheral surface of the movable shaft and fixed in a close contact state on an outer peripheral surface of the movable shaft;
a torsion absorbing portion integrally connected to the cylindrical second cover and the first cover, the torsion absorbing part being configured to absorb a torsion caused by rotation of the cylindrical second cover associated with rotation of the movable shaft;
a rubber cover made of a rubber material and having the first cover, the cylindrical second cover, and the torsion absorbing portion, and
a frame-shaped cover made of a resin material and being disposed along and over an entire periphery of an edge of the rubber cover, the frame-shaped cover being fixed in close contact on the first housing of the drive mechanism.

18. The manipulator of claim 17, further comprising:
a power transmission connected at one end thereof to the movable shaft and at an opposite end thereof to the surgical device; and
an elongated insert section extending from the first housing in a direction intersecting the rotation axis,
wherein the surgical device is disposed on a tip of the elongated insert section, and
power of the at least one motor is transmitted from the movable shaft to the surgical device via the power transmission.

19. The manipulator of claim 17, wherein the portion of the movable shaft has one of a recess or a projection.

20. A manipulator comprising:
a drive unit comprising a first housing having a plurality of motors disposed in the first housing, each of the plurality of the motors includes a first connecting portion projected outwardly from the first housing; and
a drive mechanism configured to be mounted onto the drive unit, the drive mechanism comprises a second housing having a plurality of movable shafts supported rotatably on the second housing, the plurality of movable shafts being projected outwardly from the second housing and wherein each of the plurality of movable shafts being coupled to a corresponding first connecting portion when the drive unit is engaged with the drive mechanism, and
a cover being configured to seal a gap between each of the plurality of movable shafts and the second housing so as to prevent fluid from entering the gap between each of the plurality of movable shafts and the second housing;
wherein the drive unit includes two ledge members each of which being attached to respective ends of the first housing.

21. The manipulator of claim 20, wherein the drive mechanism is attached to a surgical device to treat a body tissue.

22. The manipulator of claim 20, further comprising a power transmission configured to be connected at one end to the plurality of movable shafts and at an opposed end to a surgical device so as to transmit power from the plurality of motors to the surgical device.

23. The manipulator of claim 20, wherein the drive mechanism includes two latch members each of which being configured to engage with a corresponding one of the two ledge members when the drive mechanism and the drive unit are attached to one another.

24. A manipulator comprising:
a drive unit comprising a first housing having a plurality of motors disposed in the first housing, each of the plurality of the motors includes a first connecting portion projected outwardly from the first housing; and
a drive mechanism configured to be mounted onto the drive unit, the drive mechanism comprises a second housing having a plurality of movable shafts supported rotatably on the second housing, the plurality of movable shafts being projected outwardly from the second housing and wherein each of the plurality of movable shafts being coupled to a corresponding first connecting portion when the drive unit is engaged with the drive mechanism, and
a cover being configured to seal a gap between each of the plurality of movable shafts and the second housing so as to prevent fluid from entering the gap between each of the plurality of movable shafts and the second housing;
wherein each of the plurality of movable shafts includes a second connecting portion comprising a recess.

25. The manipulator of claim 24, wherein the drive mechanism is attached to a surgical device to treat a body tissue.

26. The manipulator of claim 24, further comprising a power transmission configured to be connected at one end to the plurality of movable shafts and at an opposed end to a surgical device so as to transmit power from the plurality of motors to the surgical device.

* * * * *